US006872387B1

(12) United States Patent
Ma

(10) Patent No.: US 6,872,387 B1
(45) Date of Patent: Mar. 29, 2005

(54) THREE-DIMENSIONAL HYDROGEL/CELL SYSTEM

(75) Inventor: Peter X. Ma, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 09/255,963

(22) Filed: Feb. 23, 1999

Related U.S. Application Data

(60) Provisional application No. 60/075,802, filed on Feb. 24, 1998.

(51) Int. Cl.[7] .......................... A01N 63/00; A61K 9/14; C12N 11/00; C12N 5/00; A61F 2/00

(52) U.S. Cl. .................... 424/93.21; 424/422; 424/423; 424/489; 435/174; 435/177; 435/182; 435/382; 523/113; 623/23.76

(58) Field of Search .............................. 424/93.21, 422, 424/423, 489, 424, 425; 435/174, 177, 182, 382; 623/23.76, 23.72; 523/113

(56) References Cited

U.S. PATENT DOCUMENTS

| | | | |
|---|---|---|---|
| 5,514,378 A | 5/1996 | Mikos et al. | ................ 424/425 |
| 5,658,329 A | 8/1997 | Purkait et al. | ............ 623/11.11 |
| 5,658,343 A | * 8/1997 | Hauselmann et al. | .......... 623/20 |
| 5,709,854 A | 1/1998 | Griffith-Cima et al. | ..... 424/93.7 |
| 5,716,404 A | 2/1998 | Vacanti et al. | .................. 623/8 |
| 5,801,033 A | 9/1998 | Hubbell et al. | .............. 435/182 |
| 5,834,001 A | 11/1998 | Dionne et al. | ............... 424/422 |
| 5,853,717 A | 12/1998 | Schinstine et al. | ........ 424/93.21 |
| 5,855,610 A | 1/1999 | Vacanti et al. | ............ 623/11.11 |
| 5,855,613 A | 1/1999 | Antanavich et al. | ...... 623/11.11 |
| 5,858,747 A | 1/1999 | Schinstine et al. | ........... 435/182 |

OTHER PUBLICATIONS

Catherine K. Kuo et al, Ionically crosslinked alginate hydrogels as scaffolds for tissue engineering: Part 1. Structure, gelation rate and mechanical properties, Biomaterials 22 (2001) 511–521.*

Xingwu Wang et al, Calcium alginate gels: formation and stability in the presence of an inert electrolyte, Polymer vol. 39, No. 13, pp. 2759–2764, 1998.*

A. Martinsen et al, Alginate as Immobilization Material: I. Correlation between Chemical and Physical Properties of Alginate Gel Beads, Biotechnology and Bioengineering, vol. 33, pp. 79–89, 1989.*

Cao et al. Book of Abstracts, 211th ACS National Meeting, New Orleans, LA, Mar. 1996.*

Draget et al, Carbohydrate Polymer 14: 159–178, 1991.*

P.X. Ma and R. Langer, "Fabrication of biodegradable polymer foams for cell transplantation and tissue engineering", vol. 18: *Tissue Engineering Methods and Protocols*, M. Yarmush and J. Morgan, Editors. 1998, Humana Press Inc.: Totowa, NJ.

P.X. Ma, B. Schloo, D. Mooney, and R. Langer, "Development of biomechanical properties and morphogenesis of in vitro tissue engineered cartilage", *J Biomed Mater Res*, 29(12): 1587–1595 (1995).

P.X. Ma and R. Langer, "Degradation, structure and properties of fibrous nonwoven poly(glycolic acid) scaffolds for tissue engineering", *Mat. Res. Soc. Symp. Proc.* vol. 394, Pittsburgh, 99–104 (1995).

P.X. Ma, T. Shin'oka, T. Zhou, D. Shum–Tim, J. Lien, J.P. Vacanti, J. Mayer, and R. Langer, "Biodegradable woven/nonwoven composite scaffolds for pulmonary artery engineering in an juvenile lamb model", *Transactions of the Society for Biomaterials*,: 295 (1997).

T. Shinoka, C. Breuer, R. Tanel, G. Zund, T. Miura, P. Ma, R. Langer, J. Vacanti, and J.E. Mayer, "Tissue engineering heart valves: valve leaflet replacement study in a lamb model", *Ann Thorac Surg*, 60(6 Suppl): S513–516 (1995).

T. Shinoka, P.X. Ma, D. Shum–Tim, C.K. Breuer, R.A. Cusick, G. Zund, R. Langer, J.P. Vacanti, and J.E. Mayer, "Tissue–engineering heart valves: Autologous valve leaflet replacement study in a lamb model", *Circulation*, 94(9 Supplement): II–164–168 (1996).

Y. Cao, J. Vacanti, X. Ma, K. Paige, J. Upton, Z. Chowanski, B. Schloo, R. Langer, and C. Vacanti, "Generation of neo–tendon using synthetic polymers seeded with tenocytes", *Transplant Proc*, 26(6): 3390–3392 (1994).

R.A. Cusick, HJ. Lee, K. Sano, J.M. Pollok, H. Utsunomiya, P.X. Ma, R. Langer, and J.P. Vacanti, "The effect of donor and recipient age on engraftment of tissue–engineered liver", *J Pediatr Surg*, 32(2): 357–360 (1997).

T.H. Kim, H.M. Lee, H. Utsonomiya, P.Ma, R. Langer, E.V. Schmidt, and J.P. Vacanti, "Enhanced survival of transgenic hepatocytes expressing hepatocyte growth factor in hepatocyte tissue engineering", *Transplant Proc*, 29(1–2): 858–860 (1997).

A. Martinsen, G. Skjak–Braek, and O. Smidsrod, "Alginate as Immobilization Material: I. Correlation between Chemical and Physical Properties of Alginate Gel Beads", *Biotechnology and Bioengineering*, 33: 79–89 (1989).

K.I. Draget, K. Ostgard, and O. Smidsrod, "Homogeneous Alginate Gels: A Technical Approach", *Carbohydrate Polymers*, 14: 159–178 (1991), even numbered pages are missing.

I.W. Cottrell and P. Kovacs, "Alginates", in *Handbook of water–soluble gums and resins*, R.L. Davidson, Editor. 1980, McGraw–Hill: New York,2–1 through 2–43.

(Continued)

Primary Examiner—Sumesh Kaushal
(74) Attorney, Agent, or Firm—Dierker & Associates, PC

(57) ABSTRACT

Methods and compositions are described that provide scaffolds for the support of cells. The scaffolds of the present invention have structural uniformity and desirable mechanical properties that make them suitable for a variety of uses, including uses for in vitro tissue regeneration or in vivo tissue or organ replacement. A method is described for controlling three-dimensional structure of the hydrogel/cell constructs under tissue culture environment.

49 Claims, 11 Drawing Sheets

OTHER PUBLICATIONS

P. Aebischer, E. Buchser, J. Joseph, J. Favre, N. de Tribolet, M. Lysaght, S. Rudnick, and M. Goddard, "Transplantation in humans of encapsulated xenogeneic cells without immunoscuppression: A preliminary report", *Transplantation,* 58(11): 1275–1277 (1994).

A. Atala, W. Kim., K. Paige, C. Vacanti, and A. Retik, "Endoscopic treatment of vesicoureteral reflux with a chondrocyte–aliginate suspension", *J Urol,* 152(2 Pt–2): 641–643; discussion 644 (1994).

K. Paige, L. Cima, M. Yaremchuk, J. Vacanti, and C. Vacanti, "Injectable cartilage", Plast Reconst. Surg, 96(6): 1390–1398; discussion 1399–1400 (1995).

Langer, Robert and Joseph P. Vacanti, "Tissue Engineering," *Science,* vol. 260; pp. 920–926; May 14, 1993.

\* cited by examiner (a)

(b)

(a) 1.75% MP alginate gels (b) 1.5% LH alginate gels (a) MP alginate gels with 1X $CaCO_3$ (b) LH alginate gels with 1.5X $CaCO_3$ (a) MP alginate gels with 1X CaCO$_3$ (b) LH alginate gels with 1.5X CaCO$_3$.

(a) 1.75% MP alginate gels.

(b) 1.5% LH alginate gels.

(a) 1.75% MP alginate gels (b) 1.5% LH alginate gels

US 6,872,387 B1

THREE-DIMENSIONAL HYDROGEL/CELL SYSTEM

The present application claims priority to U.S. Provisional Patent Application Ser. No. 60/075,802, filed Feb. 24, 1998.

FIELD OF THE INVENTION

The present invention relates to compositions and methods for growing cells in a three-dimensional hydrogel/cell system, and in particular, for growing cells for the fabrication of tissues and organs.

BACKGROUND

Every year, millions of Americans suffer tissue loss or end-stage organ failure. Approximately 8 million surgical procedures are performed annually in the United States to treat these disorders. Physicians treat organ or tissue loss by transplanting organs from one individual to another. Although transplantation is one of the life-saving therapies, it is seriously limited by donor scarcity. Tissue engineering, which aims at creating biological body parts as alternatives for transplants, offers the possibility of substantial savings by providing substitutes that are less expensive than donor organs and by providing a means of intervention before patients become critically ill (Langer and Vacanti, "Tissue engineering," Science 260: 920–926 [1993]).

One approach for tissue engineering uses tissue-inducing substances. The success of this approach depends on the purification and large-scale production of appropriate signal molecules, such as growth factors, and, in many cases, the development of methods to deliver these molecules to their targets. Another approach uses isolated cells or cell substitutes. This approach avoids the complications of surgery, allows replacement of only those cells that supply the needed function, and permits manipulation of cells before infusion.

However, isolated cells cannot form new tissues on their own. Most cells have a requirement for attachment to a surface in order to replicate and function, and require specific environments which often include the presence of supporting material to act as a template for growth. Three dimensional scaffolds are used to mimic their natural counterparts, the extracellular matrices of the body. They serve both as a physical support and as an adhesive substrate (U.S. Pat. No. 5,514,378 to Mikos et al. [1996]). Thus, scaffolding plays a pivotal role in the engineering of new tissues and organs (Ma and Langer, "Methods for the fabrication of biodegradable polymer foams for cell transplantation and tissue engineering," in Tissue Engineering Methods and Protocols, Yarmush and Morgan (eds.), Humana Press Inc.: Totowa, N.J., 1998).

Natural or synthetic polymers can be used to form highly porous scaffolds. Various tissues have been engineered from highly porous scaffolds prepared from synthetic biodegradable polymers such as poly(glycolic acid), poly(lactic acid), and poly(glycolic acid-co-lactic acid). (See e.g., Ma and Langer, supra; Ma et al., J. Biomed Mater. Res. 29: 1587–1595 [1995]; Ma et al., Ann. Thorac. Surg. 60: S513–516 [1995]; Cusick et al., J. Pediatr. Surg. 32: 357–360 [1997]; Ma et al., Transactions of the Society for Biomaterials 295 [1997]; Ma and Langer, "Degradation, structure and properties of fibrous nonwoven poly(glycolic acid) scaffolds for tissue engineering," in Polymers in Medicine and Pharmacy, Mikos et al. (eds.), pp. 99–104, MRS: Pittsburg [1995]; Shinoka et al., Circulation 94 (9 Supplement): II-164–168 [1996]; Cao et al., Transplant Proc. 26: 3390–3392 [1994]; Kim et al., Transplant Proc. 29: 858–860 [1997]). Although synthetic polymers generally give good reproducibility and controlled release kinetics compared to natural materials (See e.g., U.S. Pat. Nos. 5,855,610 and 5,716,404 to Vacanti et al.), they may not interact with cells in a desired manner (Langer and Vacanti, supra). On the other hand, natural polymers are advantageous in that they contain information (e.g., particular amino acid sequences) that facilitates cell attachment or maintenance of differentiated function (Langer and Vacanti, supra).

What is needed is a method for controlling three-dimensional structures of hydrogel/cell constructs from natural polymers, for use as highly porous scaffolds that permit the support of cells for growth.

SUMMARY OF THE INVENTION

The present invention relates to compositions and methods for growing cells in a three-dimensional hydrogel/cell system, and in particular, for growing cells for the fabrication of tissues and organs. In one embodiment, the present invention contemplates a method wherein ionically crosslinked alginate gels are used as scaffolds with defined dimensions for in vitro tissue engineering applications.

In a specific embodiment, the present invention contemplates a method for tissue engineering in vitro comprising the steps of: a) providing: i) an alginate salt, ii) a source of calcium ions, and iii) a calcium releasing compound; b) mixing the alginate salt with the source of calcium ions to provide a mixture; and c) adding calcium releasing compound to provide a three-dimensional crosslinked hydrogel system. In one embodiment, the method further comprises the step of d) culturing the three-dimensional crosslinked hydrogel system for growing cells in vitro. While the above-named components can be added together, it is preferred that the method is carried out in a stepwise fashion, such that said calcium releasing compound is added last. This has been found to produce the best results.

It is not intended that the present invention be limited by the nature of the alginate salt. Moreover, the present invention contemplates the combination of alginate materials and is not limited to one specific type of alginate salt. In one embodiment, the alginate salt is sodium alginate. In another embodiment, the alginate salt is potassium alginate. In one embodiment, the alginate salt is prepared from an alginate source selected from *Macrocystis pyrifera* and *Laminaria hyperborea*. A variety of alginates (e.g., from *Macrocystis pyrifera*) are commercially available (e.g., from Sigma, St. Louis, Mo.).

It is not intended that the present invention be limited by the nature of the source of calcium ions. In one embodiment, the source of calcium ions is calcium carbonate. In another embodiment, the source of calcium ions is calcium sulfate. In yet another embodiment, the source of calcium ions is calcium sulfate dihydrate. It is also not intended that the present invention be limited to a particular type of cation for crosslinking (i.e., calcium). In one embodiment, the present invention contemplates the use of divalent or multivalent cations as sources of cations for crosslinking. Moreover, the present invention contemplates the combination of cation sources for crosslinking.

It is not intended that the present invention be limited to the calcium releasing compound. The calcium releasing compound need simply cause the calcium source to release calcium ions, thereby initiating gelation. In one embodiment, the releasing compound comprises D-glucono-δ-lactone ($C_6H_{10}O_6$).

In one embodiment, the source of calcium ions is calcium carbonate, and the calcium-releasing compound is D-glucono-δ-lactone. Although it is not intended that the reagents be mixed using a particular ratio of reagents, the molar ratio of calcium carbonate to D-glucono-δ-lactone in one preferred embodiment is 0.5.

In yet another embodiment, the method of the present invention further comprises the step of implanting the three-dimensional crosslinked hydrogel system.

It is not intended that the three-dimensional crosslinked hydrogel system of the present invention be limited to a particular dimension. In one embodiment, the three-dimensional crosslinked hydrogel system has a thickness of between about 4 mm and about 8 mm. In another embodiment, the three-dimensional crosslinked hydrogel system has a diameter of approximately 18 mm.

It is also not intended that the three-dimensional crosslinked hydrogel system of the present invention have a particular composition. In one embodiment, the three-dimensional crosslinked hydrogel system has a calcium ion to carboxyl molar ratio of 0.27.

The present invention also contemplates the addition of other components (e.g., inert or bioactive) without affecting the methods of the present invention.

In another embodiment, the present invention contemplates a method for tissue engineering in vitro comprising the steps of: a) providing: i) cells, ii) an alginate salt, iii) a source of calcium ions, and iv) a calcium releasing compound; b) mixing the cells, alginate salt, and the source of calcium ions to provide a mixture; c) adding the calcium releasing compound to the mixture to provide a crosslinked gel; and d) culturing the crosslinked gel to provide a three-dimensional crosslinked hydrogel/cell system for growing cells in vitro.

In one embodiment, the alginate salt is selected from the group consisting of sodium alginate and potassium alginate. In another embodiment, the alginate salt is prepared from an alginate source selected from *Macrocystis pyrifera* and *Laminaria hyperborea*. In yet another embodiment, the source of calcium ions is selected from the group consisting of calcium carbonate and calcium sulfate. In an alternative embodiment, the calcium releasing compound is D-glucono-δ-lactone.

In one embodiment, the source of calcium ions is calcium carbonate, and the calcium releasing compound is D-glucono-δ-lactone, and the molar ratio of calcium carbonate to D-glucono-δ-lactone in one preferred embodiment is 0.5.

In another embodiment, the method further comprises the step of implanting said three-dimensional crosslinked hydrogel/cell system.

In one embodiment, the three-dimensional crosslinked hydrogel/cell system has a thickness of between about 4 mm and about 8 mm, and a diameter of approximately 18 mm. In another embodiment, the three-dimensional crosslinked hydrogel/cell system has a calcium ion to carboxyl molar ratio of 0.27.

It is not intended that the present invention be limited for culturing particular type of cells (or merely one cell type on a scaffold). A variety of cell types (including mixtures of different cells) are contemplated. In one embodiment, the cells are osteoblasts. In another embodiment, the cells secrete a medically useful compound (e.g., hormone, cytokine, etc.). Such cells may be (but need not be) cells that have been manipulated by recombinant means to secrete such compounds.

Finally, the present invention also contemplates the resulting crosslinked alginate gel as a composition. Moreover, the present invention contemplates the resulting crosslinked gel in combination with other components, such as cells. It is not intended that the cells be limited to particular cell type, or merely one cell type on a scaffold. A variety of cell types, including mixtures of different cells, are contemplated.

Definitions

To facilitate understanding of the invention, a number of terms are defined below.

The present invention contemplates implanting crosslinked gels into hosts. The term "host" refers to both humans and animals.

"Initiating a reaction" means causing a reaction to take place. Reactions can be initiated by any means (e.g., heat, wavelengths of light, addition of a catalyst, etc.) The present invention contemplates "initiating gelation" by addition of a calcium releasing compound to the above-described mixture, said mixture comprising a source of calcium ions.

As used herein, the term "implant" and "implanting" and the like indicates placement on, in, or through a patient's body (including placement in body cavities) in the course of medical treatment, e.g., for a disease, impairment or injury. Implants include, but are not limited to, implants for wound care, drug delivery, and bone replacement.

As used herein, the term "hydrogel" refers to a three-dimensional network of cross-linked hydrophilic polymers in the form of a gel substantially composed of water, and preferably, but not limited to gels. Hydrogels may have a net positive or negative charge, or may be neutral. A typical net negative charged matrix is alginate. Hydrogels carrying a net positive charge may be typified by extracellular matrix components such as collagen and laminin. An example of a net neutral hydrogel is highly crosslinked polyethylene oxide of polyvinyl alcohol.

As used herein, the term "crosslinked" or "cross-linking" refers to an attachment of two chains of polymer molecules by bridges, composed of either an element, a group, or a compound, that join certain atoms of the chains by primary chemical bonds. For example, polysaccharide molecules can cross-link to form stable gel structures (i.e., dextran). Cross-linking can also be effected artificially, such as by adding a chemical substance (i.e., a cross-linking agent) and exposing the mixture to heat, or by subjecting the polymer to high-energy radiation.

As used herein, the term "alginate" refers to any of several derivatives of alginic acid (e.g., calcium, sodium, or potassium salts or propylene glycol alginate). These compounds are hydrophilic colloids obtained from seaweed.

DESCRIPTION OF THE INVENTION

Figure 1:
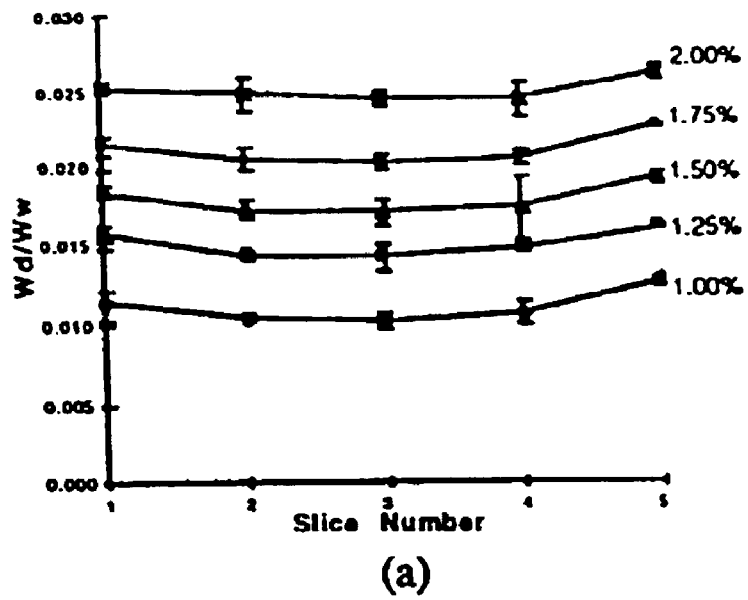
FIGS. 1a-1b is a graph showing the dry to wet weight ratios of MP alginate gels with varying alginate concentrations and 1×CaCO$_3$.
Figure 1:
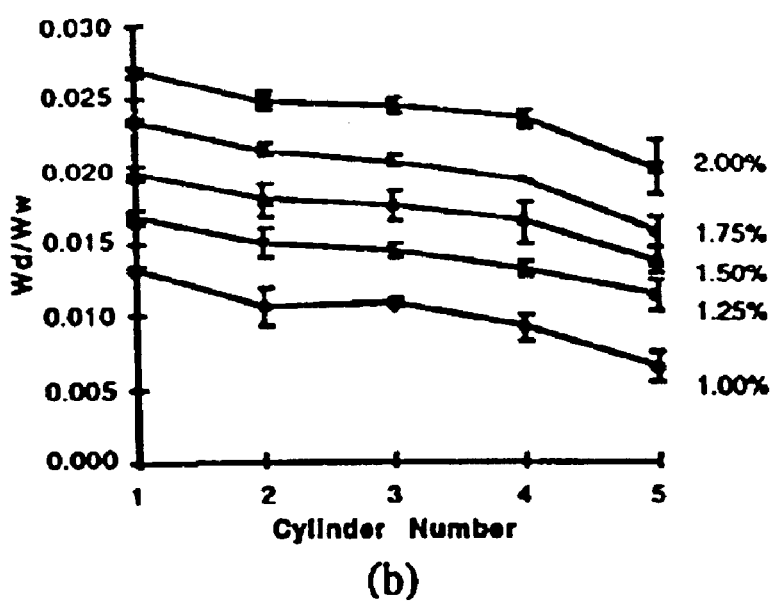

The present invention relates to compositions and methods for growing cells in a three-dimensional hydrogel/cell system, and in particular, for growing cells for the fabrication of tissues and organs. The present invention demonstrates that alginates from various sources can be ionically crosslinked to form gels. Their structural stability, mechanical properties can be controlled by alginate source and concentration, calcium ion source and concentration, and gel preparation methods.

The methods of the present invention permit the formation and preparation of structurally homogeneous and mechanically strong alginate gels with defined dimensions, which can be used to incorporate living cells. The three dimensional gel structure with incorporated cells can be maintained in an in vitro tissue culture environment by adjusting calcium ion concentration in the culture medium. These results have demonstrated how ionically crosslinked alginate gels with defined three dimensional structure can be reliably used as a tissue engineering scaffold.

The scaffolds can be maintained in vitro as well as implanted in a host. After fulfilling the purpose as a matrix or scaffold, the hydrogels of the present invention can be dissolved or degraded, leaving nothing behind except the regenerated new tissues or organs. Because of the abundance in material sources, low prices, and easy processing, the system makes large-scale tissue engineering/manufacture feasible.

Alginic acid, a polysaccharide from seaweeds, is a family of natural copolymers of β-D-mannuronic acid and α-L-guluronic acid (Martinsen et al., Biotechnology and Bioengineering 33: 79–89 [1989]; Draget et al., Carbohydrate Polymers 14: 159–178 [1991]. Because of their biocompatibility, abundance in source, and low prices, they have been widely used in food industry as thickeners and emulsifying agents. They have also been processed into gel beads encapsulating living cells as a means of immunoprotection. (See e.g., Cottrell and Kovacs, "Alginates," in Handbook of water-soluble gums and resins," Davidson (ed.), McGraw-Hill: New York [1980]; Aebischer et al., Transplantation 58: 1275–1277 [1994]; U.S. Pat. No. 5,834,001 to Dionne et al.).

Alginate gels have not been reported as scaffolds to engineer tissues in vitro, probably due to the difficulties in controlling the mechanical properties, shape and size in a cell culture environment. The present invention describe methods and compositions related to the use of ionically crosslinked alginate gels as scaffolds with defined dimensions for in vitro tissue engineering applications, that are controlled and reproducible.

Experimental

The following examples serve to illustrate certain preferred embodiments and aspects of the present invention and are not to be construed as limiting the scope thereof.

I. Materials

Sodium alginate prepared from *Laminaria hyperborea* (LH), Protanal LF200, was from Pronova Biopolymer (Drammen, Norway). High viscosity sodium alginate prepared from *Macrocystis pyrifera* (MP), calcium carbonate ($CaCO_3$), calcium chloride dihydrate ($CaCl_2.2H_2O$), calcium sulfate dihydrate ($CaSO_4.2H_2O$), D-glucono-δ-lactone ($C_6H_{10}O_6$) (GDL), L-ascorbic acid, dimethyl sulfoxide, and trypsin-EDTA were from Sigma (St. Louis, Mo.). Dulbecco's modified Eagle's medium (DMEM) and phosphate-buffered saline (DPBS), fetal bovine serum (FBS), and penicillin-streptomycin (P/S) were from GibcoBRL (Grand Island, N.Y.). MC3T3-E1 osteoblasts were kindly provided by Dr. R. Franceschi (University of Michigan School of Dentistry).

II. Methods

A. Gel Preparation

Sodium alginate was dissolved in either deionized water or a tissue culture medium. Either calcium sulfate ($CaSO_4$) or calcium carbonate ($CaCO_3$) in combination with GDL was used as a source of calcium ions to initiate gelation. When $CaCO_3$ was used, a $CaCO_3$ to GDL molar ratio of 0.5 was always maintained to achieve a neutral pH value. For all alginate solutions, a basic calcium ion to carboxyl molar ratio of 0.18 (a 36% crosslinking density for the carboxyl groups if a 100% crosslinking efficiency were achieved) was designated as 1×. The crosslinking density was adjusted with a multiplication factor to this molar ratio as a relative calcium ion content, such as 0.5× (molar ratio: 0.09), 1.5× (molar ratio: 0.27), 2× (molar ratio: 0.36), and so forth. Sodium alginate solution was added to $CaCO_3$ suspension, mixed and vortexed for one minute. A fresh aqueous GDL solution was then added to the suspension and vortexed for one minute to initiate gelation. When calcium sulfate was used as a source of calcium ions, calcium sulfate dihydrate ($CaSO_4.2H_2O$) was dispersed in either deionized water or tissue culture medium. The suspension was added to sodium alginate solution and vortexed for 15 seconds. These gels were prepared in Teflon vials with dimensions of 20 mm deep and 18 mm in diameter to form circular discs, approximately 8 mm thick and 18 mm in diameter. The vials were capped, sealed with Parafilm and stored in high humidity at room temperature for 48 hours of gelation. The indicated alginate gel concentrations in this paper were the final weight/volume concentrations.

B. Homogeneity

Homogeneity of the cylindrical alginate gels was characterized with the dry to wet weight ratio against position in both axial and radial directions. Gels (8 mm thick) were cut perpendicular to the cylinder axis into 5 slices with approximately the same thickness. The slices were labeled 1 through 5 from top to bottom. After measuring their wet weights, the slices were dried at 40° C. for 24 hours. The specimens were weighed again after drying and their dry/wet weight ratios were calculated. The averages and the standard deviations of triplets were reported. The homogeneity in radial direction was characterized with the dry to wet weight ratio of concentric hollow cylinders cored out of the gels (4 hollow cylinders in addition to the cylindrical core of each gel, labeled 1 through 5 from the circumference to the center). Their diameters (OD-ID) were approximately: 18.0–13.3, 13.3–12.1, 12.1–7.2, 7.2–4.1, and 4.1–0 mm respectively.

C. Mechanical Testing

Uniaxial compression was performed to measure the mechanical properties of the alginate gels with an Instron 4502 mechanical tester (Instron Corporation, Canton, Mass.) at a crosshead speed of 4.8 mm/min. The specimens were coated with silicone oil (Aldrich, Milwaukee, Wis.) to reduce the effect of friction between the gel and the plates during compression. Eight specimens (8 mm thick and 18 mm in diameter) were tested for each sample. Averages ± standard deviations were reported.

D. Swelling Ratio

One gel disc (8 mm thick and 18 mm in diameter) was immersed in 15 ml swelling solution. For water or saline based swelling solutions, the swelling experiments were carried out at room temperature in high humidity to reduce the effects of evaporation. For tissue culture medium based swelling solutions, the swelling experiments were carried out in a humidified incubator at 37° C. with 5% $CO_2$. The solutions were changed every other day. At the scheduled times, the specimens were picked up with a spatula and all the surfaces were quickly blotted on a Kimwipe tissue for two times. The specimens were weighed with an analytical balance accurate to $10^{-4}$ g. The whole process for each specimen was done within one minute to minimize the effects of evaporation. For each sample, triplets were tested to calculate the average values and standard deviations.

E. Cell Incorporation and Cultivation

MC3T3-E1 osteoblasts were cultured and expanded in tissue culture medium (89% DMEM containing 4500 mg/L D-glucose, 10% FBS, 1% P/S). The cultured cells were trypsinized with trypsin-EDTA and washed twice with DPBS. The cells were then suspended in sodium alginate solutions in "complete medium" (89% DMEM, 10% FBS, 1% P/S, and 50 mg/L L-ascorbic acid) at a density of $6.7 \times 10^6$ cells/ml. The cell-containing sodium alginate solution was added to $CaCO_3$ suspension in Teflon vials to form circular discs 4 mm thick and 18 mm in diameter, to which a fresh aqueous GDL solution was then added to initiate the gelation. They were kept in a humidified incubator to gel at 37° C. in the presence of 5% $CO_2$. The vial walls were notched at the top to allow air circulation when capped. After 48 hours, the gels were transferred to 60×15 mm petri dishes and cultured in 15 ml "complete medium" supplemented with calcium chloride to obtain an desired calcium ion concentration. The whole preparation was done in a biological safety cabinet (Model 1184, Forma Scientific, Inc., Marietta, Ohio), with aseptic techniques. Everything involved (apparatus, tools, chemicals and so on) was sterile. The medium was changed every other day.

F. Histology

Histologic specimens of cell-alginate constructs were embedded in paraffin, and cut into 5 mm cross sections for hematoxylin and eosin, Masson's trichrome, or von Kossa stained analyses.

III. Results and Discussion

One of the requirements of compressive testing was that the surfaces of the gels be flat and parallel. In some cases, the calcium source reacted with the polymer too quickly for the surfaces of the gels to level, resulting in lumpy gels (Table 1). Mechanical properties of gels prepared with different alginates and calcium ion sources of the same polymer concentration and the same relative calcium content were compared (Table 1). LH alginate gels prepared with $CaCO_3$-GDL was were the strongest of the tested gels.

TABLE 1

Comparison of alginate gels prepared from different alginate and calcium sources of the same alginate concentration (1.5%) and calcium content (1.5X).

| Alginate Source | Calcium Source | Compressive Strength (kPa) | Compressive Modulus (kPa) | Appearance |
|---|---|---|---|---|
| M. pyrifera | $CaSO_4.2H_2O$ | 13.3 ± 4.50 | 7.49 ± 2.33 | lumpy |
| L. hyperborea | $CaSO_4.2H_2O$ | 36.6 ± 17.1 | 5.55 ± 2.55 | soft |
| L. hyperborea | $CaCO_3$ | 161 ± 9.72 | 22.4 ± 4.17 | strong |

A. Homogeneity

The homogeneity of cylindrical alginate gels was characterized with the dry/wet weight ratio in both axial and radial directions. MP alginate gels with varying polymer concentrations (1.00, 1.25, 1.50, 1.75, 2.00%) were prepared with 1×$CaCO_3$. Horizontally sliced sections and vertically cored hollow cylinders exhibited comparable homogeneity profiles for all five alginate concentrations (FIGS. 1a and 1b). This indicated that the polymer concentration did not have significant effects on the gel homogeneity in the concentration range studied. In the axial direction, the dry/wet weight ratio was almost the same everywhere except for the bottom slice. The slightly higher ratio of the bottom slice was likely due to either adherence of the $CaCO_3$ powder to the bottom during mixing or some sedimentation during the gelation. In the radial direction, the dry/wet weight ratio decreased slightly from circumference to the center.

B. Syneresis

Figure 2:
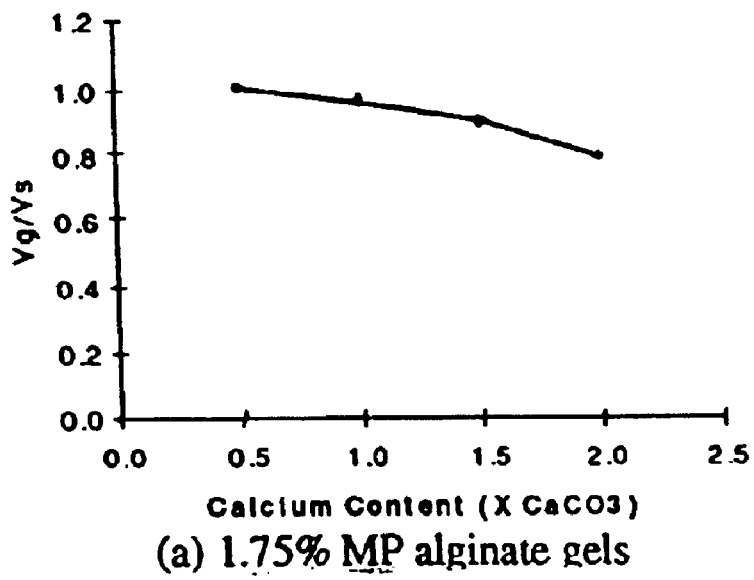
FIGS. 2a-2b is a graph showing the volume ratios of a gel to the alginate suspension to form the gel (gelation time 48 hours) versus calcium content.
Figure 2:
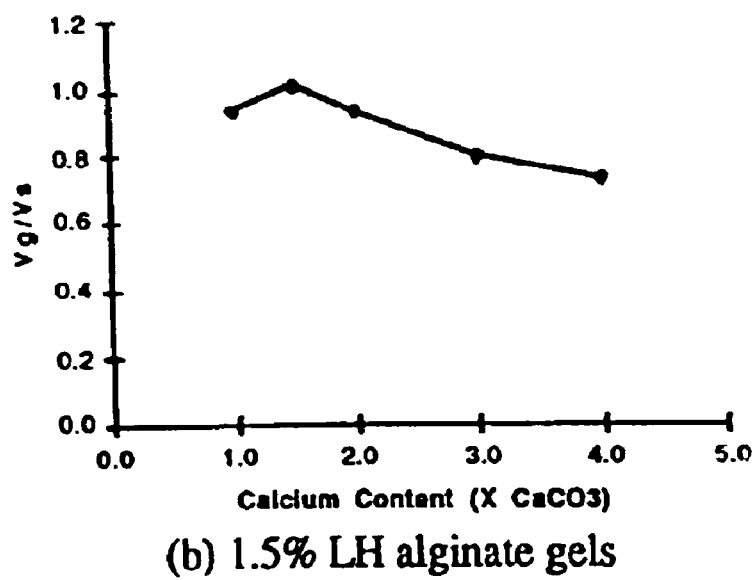
Figure 3:
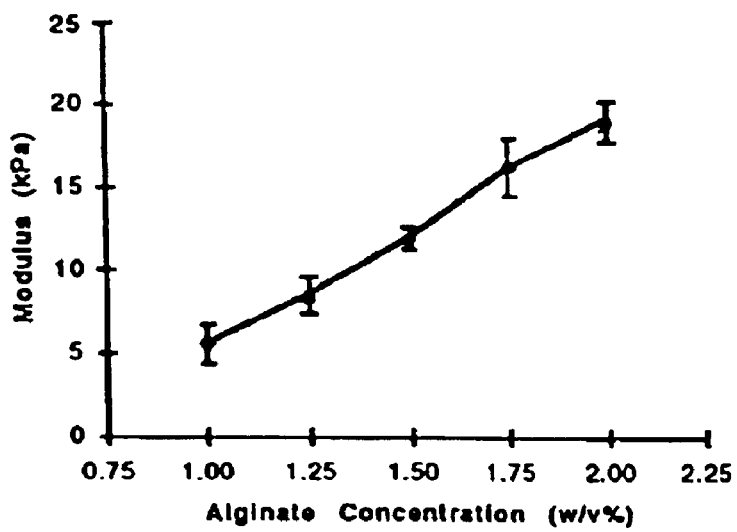
FIGS. 3a-3b is a graph showing the compressive modulus of alginate gels versus alginate concentration.
Figure 3:
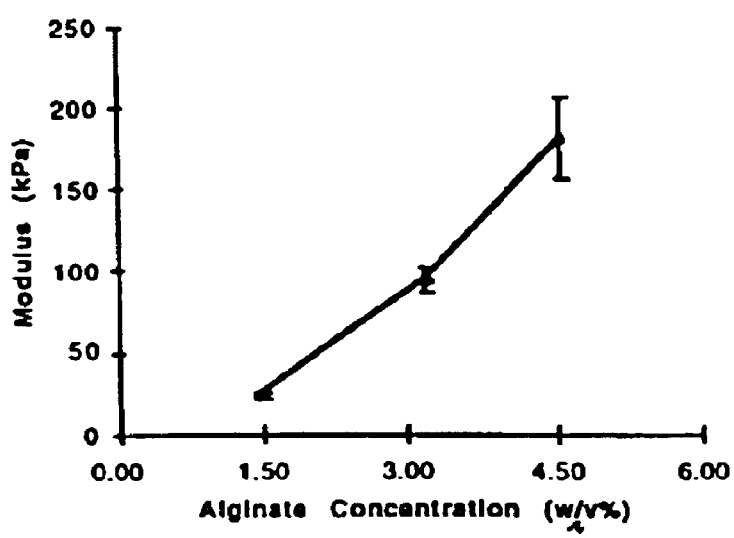

Syneresis was characterized with the volume ratio of a gel to the suspension before gelation. The gels studied were MP alginate gels prepared with a polymer concentration of 1.75% and varying relative calcium ion contents (0.5, 1.0, 1.5 and 2.0×$CaCO_3$), and LH alginate gels prepared with a polymer concentration of 1.50% with varying relative calcium ion contents (1.0, 1.5, 2.0, 3.0, and 4.0×$CaCO_3$). The general trend was that the shrinkage increased with calcium concentration (FIGS. 2a and 2b). It was assumed that an increased calcium content enhanced the inter-molecular and intra-molecular interactions of an alginate gel, shortened the average distance between ionic crosslinks, and resulted in a higher shrinkage.

C. Mechanical Properties

One of the requirements for compressive testing was that the surfaces of the gels be flat and parallel. $CaSO_4.2H_2O$ reacted with the polymer too quickly for the surfaces of the gels to level, resulting in lumpy gels. The $CaCO_3$-GDL system, on the other hand, allowed enough time for proper mixing of the suspension and leveling of the surfaces. When $CaSO_4.2H_2O$ was used, gels were prepared slightly thicker and cut to 8 mm thick to obtain the flat and parallel surfaces for mechanical testing.

Figure 8A:
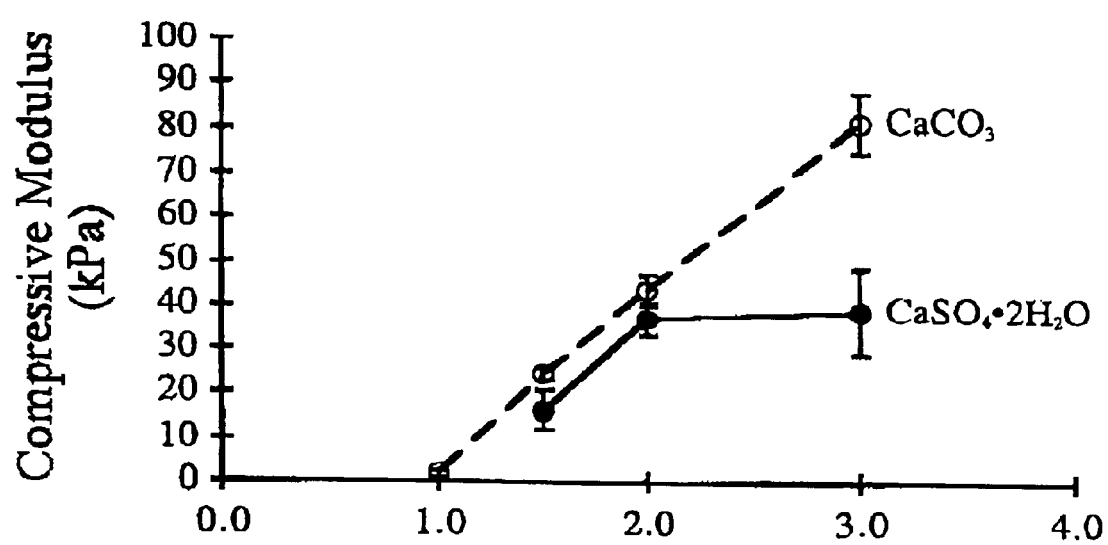
FIGS. 8a-8d show the compressive modulus strengths of alginate gels versus alginate concentration.
Figure 8B:
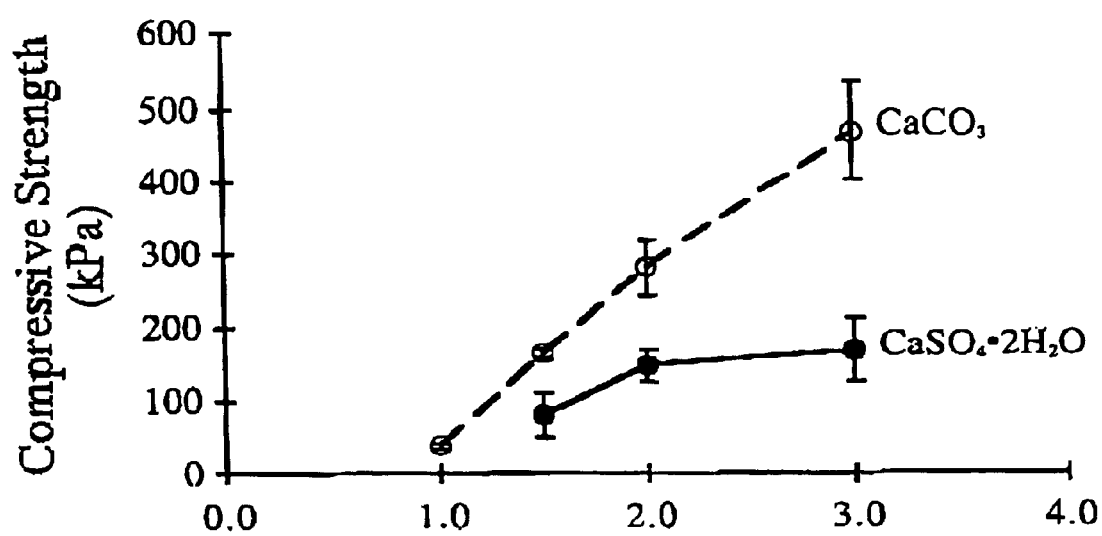
Figure 8C:
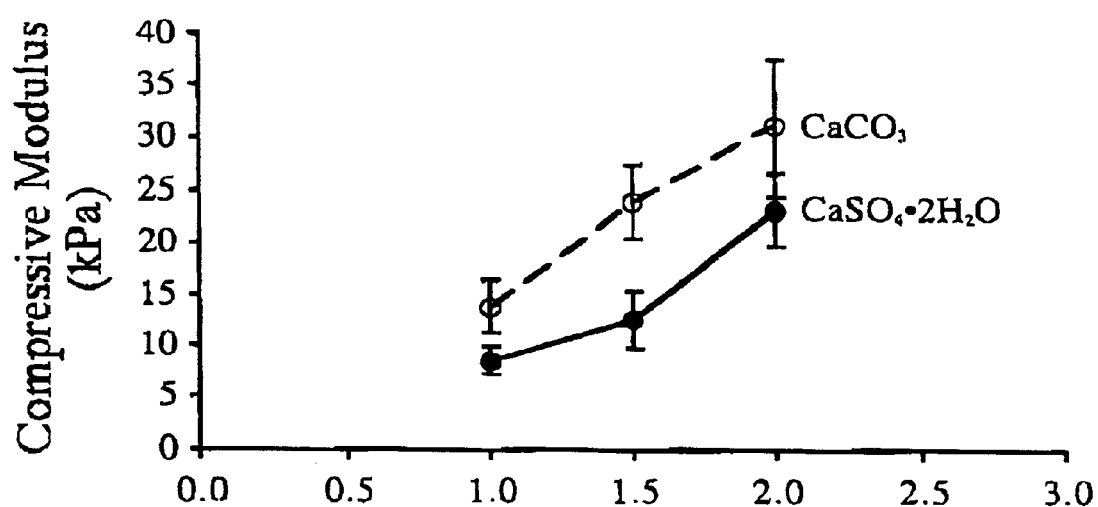
Figure 8D:
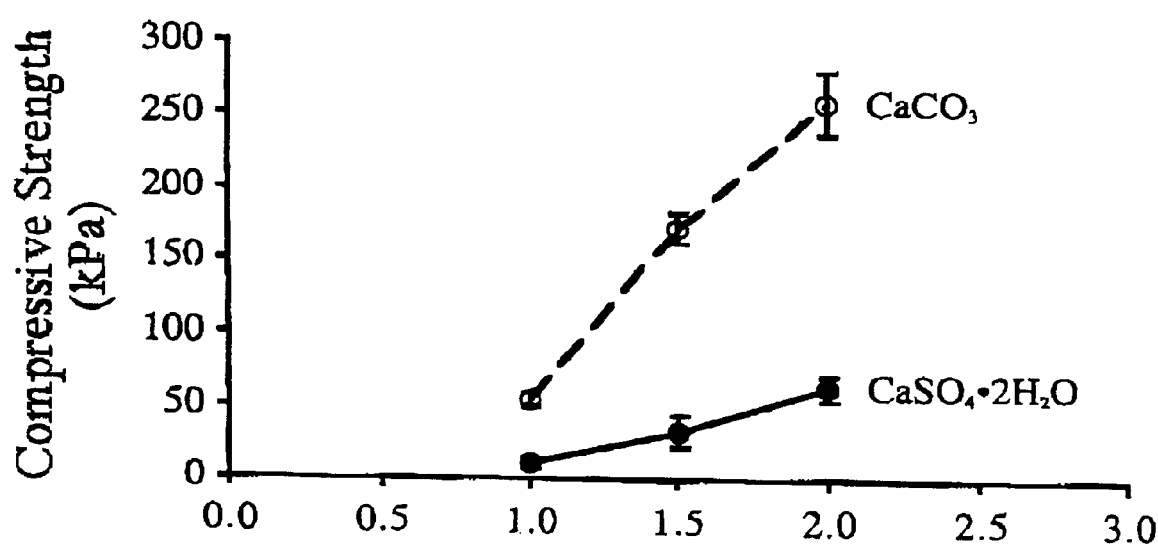

Gels made with 1.5% MP alginate and varying concentrations of $CaCO_3$ were compared to those made with varying concentrations of $CaSO_4.2H_2O$ (FIGS. 8a and 8b). The uniform gels made with $CaCO_3$ possessed greater modulus and strength than those made with $CaSO_4.2H_2O$. Similar results were found with LH alginate gels (FIGS. 8c and 8d).

Figure 4:
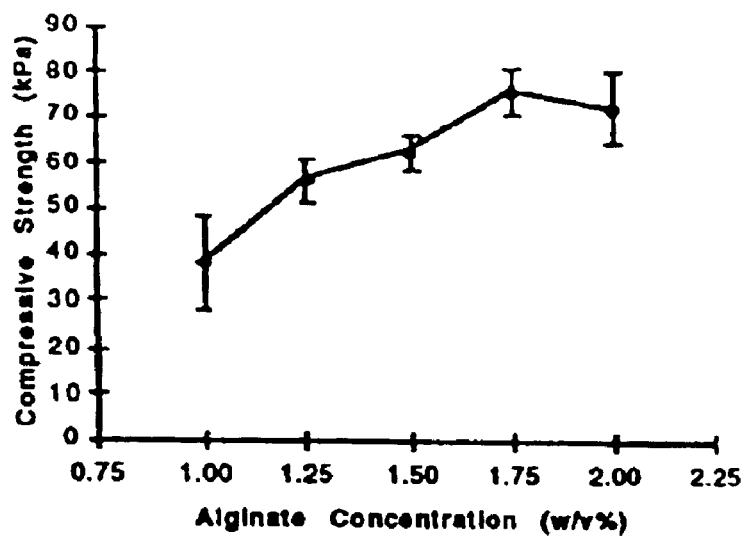
FIGS. 4a-4b is a graph showing the compressive strength of alginate gels versus alginate concentrations
Figure 4:
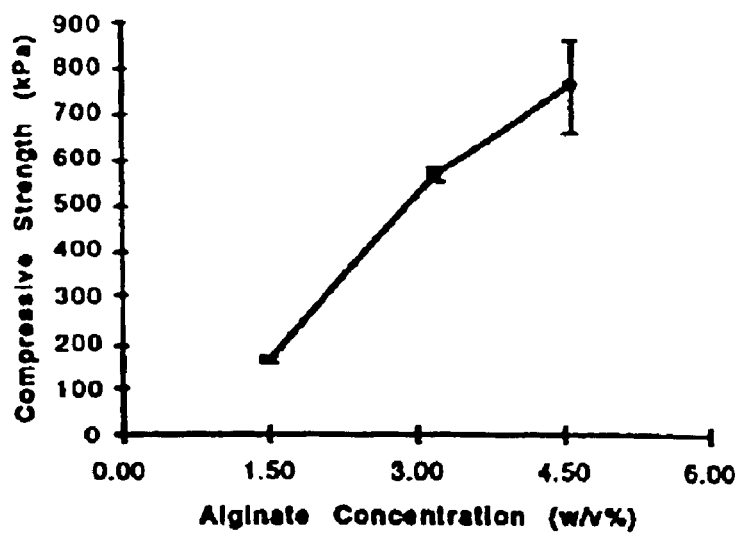
Figure 5:
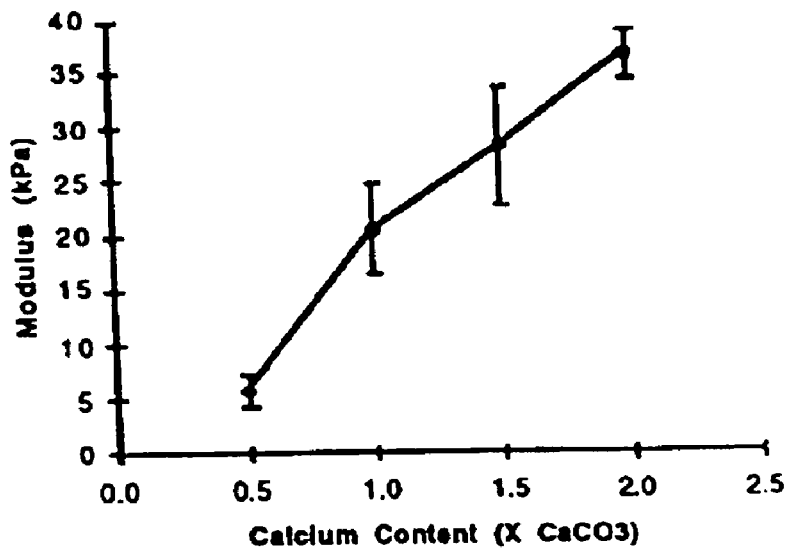
FIGS. 5a-5b is a graph showing the compressive modulus of alginate gels versus calcium content.
Figure 5:
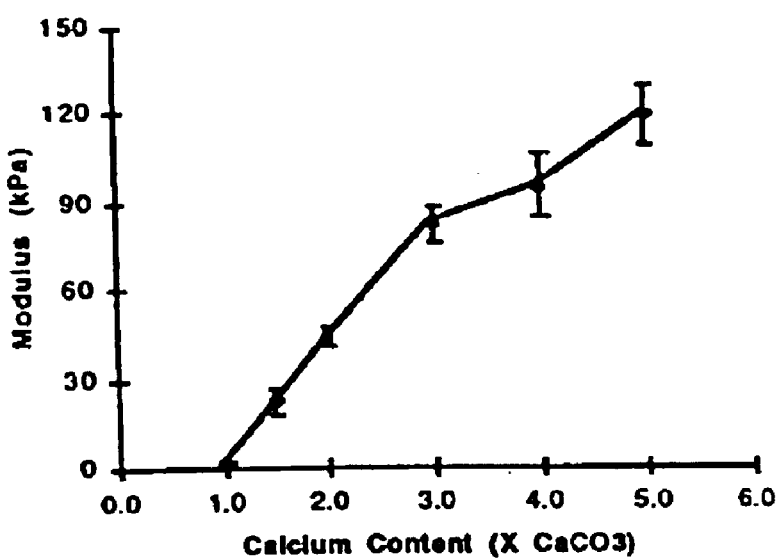
Figure 6:
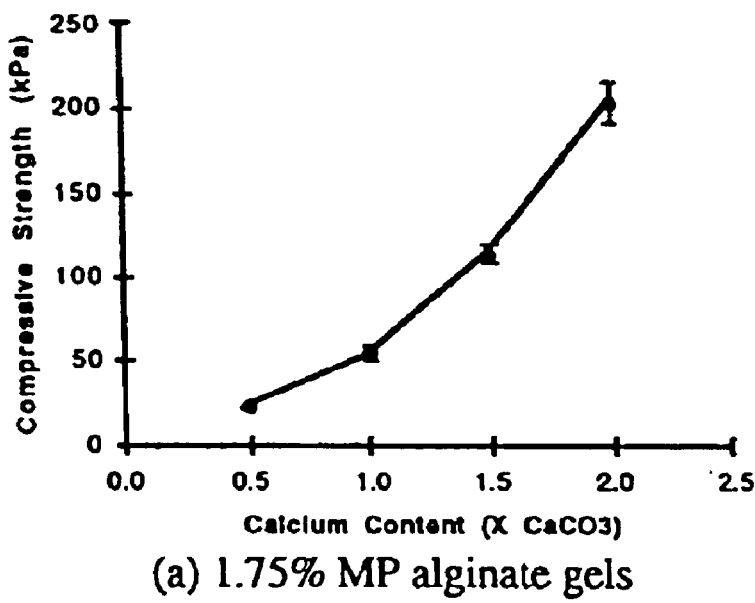
FIGS. 6a-6b is a graph showing the compressive strength of alginate gels versus calcium content.
Figure 6:
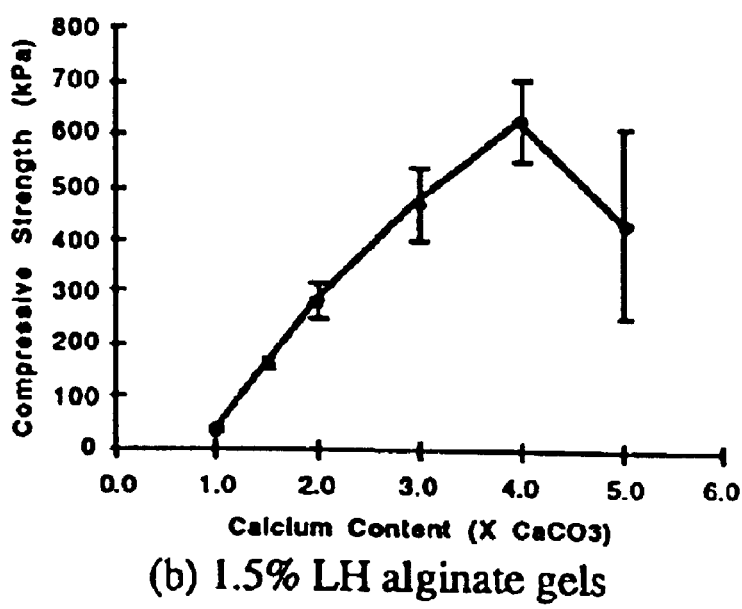

Mechanical properties of the alginate gels changed with structural variables. The compressive modulus and the compressive strength increased with alginate concentration in general (FIGS. 3a, 3b, 4a and 4b). However, the compressive strength of a MP alginate gel of 2.0% concentration was slightly lower than that of a gel of 1.75% concentration (FIG. 4a). The MP alginate solution with concentrations of 2.0% and higher were extremely viscous and difficult to work with. The fall in strength at this high alginate concentration was attributed to the poor mixing and the heterogeneous crosslinking network. The compressive modulus and the compressive strength increased with the relative calcium content (FIGS. 5a, 5b, 6a and 6b) presumably due to increased crosslinking density. However, for the gels prepared from 1.5% LH alginate, the compressive strength of the gel with a relative calcium content of 5× was lower than that of the gel with a relative calcium content of 4× (FIG. 6b). Precipitate was undetectable in the gels with 3× and lower $CaCO_3$ contents. At 4× and higher calcium content, precipitates were visible likely due to oversaturation. The decrease in compressive strength at 5× was attributed to the precipitation which might result in structural heterogeneity and stress concentrations, leading to lower average strength. The large standard deviation at 5× was another indication of the structural heterogeneity.

D. Swelling Ratio

Figure 7:
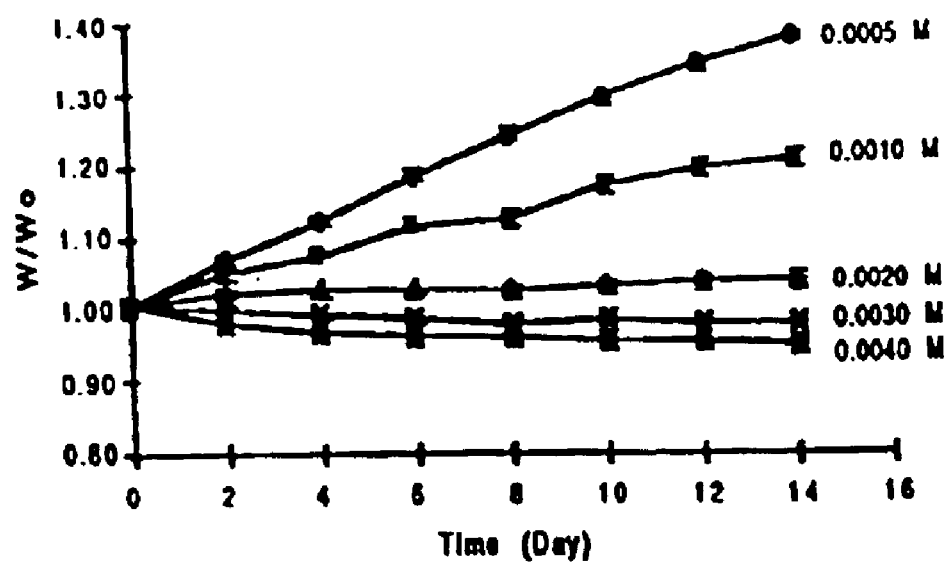
FIG. 7 is a graph showing the swelling ratio of 3.18% LH alginate gels with 1.5×CaCO$_3$ in saline.

One of the major concerns in using alginate gels as scaffolds for in vitro tissue engineering was the structural instability of the hydrogels in a tissue culture environment. The swelling experiments were designed to understand how the ionically crosslinked alginate gels behave in various aqueous solutions, and to develop ways to control the shape and size of the gels in a tissue culture environment. Sets of three circular gel discs prepared from 3.18% LH alginate with 1.5×$CaCO_3$ were immersed in saline (0.9% NaCl aqueous solution) adjusted to varying calcium ion concentrations (FIG. 7). The alginate gels swelled when the calcium ion concentration was low (0.0005 and 0.0010 M) while the gels shrank when the calcium ion concentration was high (0.0040 M). At calcium ion concentrations of 0.0020 and 0.0030 M, there was nearly no change in the gel weight over a two-week immersion experiment. Swelling experiments were also conducted with the gels (3.18% LH alginate with 1.5×$CaCO_3$) in "complete medium" adjusted to varying calcium concentrations. Again, the gels swelled at low calcium ion concentrations, but shrank at high calcium concentrations (data not shown). At a calcium concentration of 0.0030 M, the gel weight did not change significantly over immersion time. These results clearly showed that the size of ionically crosslinked alginate gels were controlled by the ion concentration of the medium.

E. Cell Incorporation and Cultivation

MC3T3-E1 osteoblasts were successfully incorporated into LH alginate gels with a polymer concentration of 3.18% and 1.5×$CaCO_3$. The complete medium was adjusted to a calcium concentration of 0.0030 M to control the gel size. Histological slides showed that the cells were uniformly distributed in the gels, assuming a spherical shape.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method comprising the steps of:
   mixing an alginate salt and a source of calcium ions to provide a mixture; adding a calcium releasing compound to the mixture to provide a three-dimensional crosslinked hydrogel system; and
   selectively controlling shrinking, swelling or maintaining of the hydrogel system by varying a calcium ion concentration of a separate medium into which the hydrogel system is introduced;
   wherein the hydrogel system swells at calcium ion concentrations in the medium between about 0.0005 M and about 0.0010 M; wherein the hydrogel system shrinks at a calcium ion concentration in the medium of about 0.0040 M; and wherein the hydrogel system remains substantially the same size at calcium ion concentrations in the medium between about 0.0020 M and about 0.0030 M.

2. The method of claim 1, further comprising the step of culturing the three-dimensional crosslinked hydrogel system in the medium for growing cells in vitro.

3. The method of claim 1, wherein the alginate salt is selected from the group consisting of sodium alginate and potassium alginate.

4. The method of claim 1, wherein the alginate salt is prepared from an alginate source selected from *Macrocystis pyrifera* and *Laminaria hyperborea*.

5. The method of claim 1, wherein the source of calcium ions is selected from the group consisting of calcium carbonate, calcium sulfate, and calcium sulfate dihydrate.

6. The method of claim 1, wherein the calcium releasing compound is D-glucono-δ-lactone.

7. The method of claim 1, wherein the source of calcium ions is calcium carbonate and the calcium releasing compound is D-glucono-δ-lactone, and wherein the molar ratio of the calcium carbonate to the D-gluconoδ-lactone is 0.5.

8. The method of claim 1, further comprising the step of implanting the three-dimensional crosslinked hydrogel system.

9. The method of claim 1, wherein the three-dimensional crosslinked hydrogel system has a thickness of between about 4 mm and about 8 mm, and a diameter of approximately 18 mm.

10. The method of claim 1, wherein the three-dimensional crosslinked hydrogel system has a calcium ion to carboxyl molar ratio of 0.27.

11. A method for tissue engineering in vitro, the method comprising the steps of:
    mixing cells, an alginate salt and a source of calcium ions to provide a mixture;
    adding a calcium releasing compound to the mixture to provide a crosslinked hydrogel;
    selectively controlling shrinking, swelling or maintaining of the crosslinked hydrogel by varying a calcium ion concentration of a separate medium into which the crosslinked hydrogel is introduced; and
    culturing the crosslinked hydrogel in the medium to provide a three-dimensional crosslinked hydrogel/cell system for growing the cells in vitro;
    wherein the hydrogel system swells at calcium ion concentrations in the medium between about 0.0005 M and about 0.0010 M; wherein the hydrogel system shrinks at a calcium ion concentration in the medium of about 0.0040 M; and wherein the hydrogel system remains substantially the same size at calcium ion concentrations in the medium between about 0.0020 M and about 0.0030 M.

12. The method of claim 11, wherein the alginate salt is selected from the group consisting of sodium alginate and potassium alginate.

13. The method of claim 11, wherein the alginate salt is prepared from an alginate source selected from *Macrocystis pynfera* and *Laminaria hyperborea*.

14. The method of claim 11, wherein the source of calcium ions is selected from the group consisting of calcium carbonate calcium sulfate, and calcium sulfate dihydrate.

15. The method of claim 11, wherein the calcium releasing compound is D-glucono-δ-lactone.

16. The method of claim 11, wherein the source of calcium ions is calcium carbonate and the calcium releasing compound is D-glucono-δ-lactone, and wherein the molar ratio of the calcium carbonate to the D-glucono-δ-lactone is 0.5.

17. The method of claim 11, further comprising the step of implanting the three-dimensional crosslinked hydrogel/cell system.

18. The method of claim 11, wherein the three-dimensional crosslinked hydrogel/cell system has a thickness of between about 4 mm and about 8 mm, and a diameter of approximately 18 mm.

19. The method of claim 11, wherein the three-dimensional crosslinked hydrogel/cell system has a calcium ion to carboxyl molar ratio of 0.27.

20. The method of claim 11, wherein the cells are osteoblasts.

21. A method for preparing a three-dimensional hydrogel system, the method comprising the steps of:
adding a calcium-releasing compound to a mixture of at least one hydrophilic polymer comprising an alginate salt and a source of calcium cations to provide a three-dimensional crosslinked hydrogel system; and
selectively controlling shrinking, swelling or maintaining of the hydrogel system by varying a calcium ion concentration of a separate medium into which the hydrogel system is introduced;
wherein the hydrogel system swells at calcium ion concentrations in the medium between about 0.0005 M and about 0.0010 M; wherein the hydrogel system shrinks at a calcium ion concentration in the medium of about 0.0040 M; and wherein the hydrogel system remains substantially the same size at calcium ion concentrations in the medium between about 0.0020 M and about 0.0030 M.

22. The method as defined in claim 21 wherein the alginate salt is selected from the group consisting of sodium alginate and potassium alginate.

23. The method as defined in claim 21, wherein the source of calcium ions is selected from the group consisting of calcium carbonate, calcium sulfate, and calcium sulfate dihydrate.

24. The method as defined in claim 23 wherein the calcium releasing compound is D-glucono-δ-lactone.

25. The method as defined in claim 24 wherein the source of calcium ions is calcium carbonate, and wherein the molar ratio of the calcium carbonate to the D-gluconoδ-lactone is 0.5.

26. The method as defined in claim 21 wherein the three-dimensional crosslinked hydrogel system has a calcium ion to carboxyl molar ratio ranging between about 0.09 and about 0.9.

27. The method as defined in claim 26 wherein the calcium ion to carboxyl molar ratio ranges between about 0.18 and about 0.72.

28. The method as defined in claim 21, further comprising the step of culturing the three-dimensional crosslinked hydrogel system in the medium for growing cells in vitro.

29. A three-dimensional crosslinked hydrogel composition, consisting essentially of:
at least one hydrophilic polymer comprising an alginate salt;
a source of calcium cations;
a calcium-releasing compound, whereby a mixture of the at least one hydrophilic polymer, the source of calcium cations and the calcium-releasing compound forms the crosslinked hydrogel composition; and
a separate culture medium into which the hydrogel composition is introduced, the culture medium having a predetermined calcium ion concentration, wherein the predetermined calcium ion concentration determines the shrinking, swelling or maintaining of the crosslinked hydrogel composition;
wherein the hydrogel system swells at calcium ion concentrations in the medium between about 0.0005 M and about 0.0010 M; wherein the hydrogel system shrinks at a calcium ion concentration in the medium of about 0.0040 M; and wherein the hydrogel system remains substantially the same size at calcium ion concentrations in the medium between about 0.0020 M and about 0.0030 M.

30. The composition as defined in claim 29, wherein the alginate salt is selected from the group consisting of sodium alginate and potassium alginate; wherein the source of calcium cations is selected from the group consisting of calcium carbonate, calcium sulfate, and calcium sulfate dihydrate; and wherein the calcium-releasing compound is D-glucono-δ-lactone.

31. The composition as defined in claim 30 wherein the source of calcium ions is calcium carbonate, and wherein the molar ratio of the calcium carbonate to the D-glucono-δ-lactone is 0.5.

32. The composition as defined in claim 30 wherein the three-dimensional crosslinked hydrogel system has a calcium ion to carboxyl molar ratio ranging between about 0.09 and about 0.9.

33. The composition as defined in claim 32 wherein the calcium ion to carboxyl molar ratio ranges between about 0.18 and about 0.72.

34. The composition as defined in claim 29 wherein when the predetermined calcium ion concentration is between about 0.0020 M and about 0.0030 M, the hydrogel composition remains substantially the same size.

35. The method of claim 2 wherein the cells secrete a medically useful compound.

36. The method of claim 11 wherein the cells secrete a medically useful compound.

37. The method of claim 28 wherein the cells are at least one of osteoblasts and cells which secrete a medically useful compound.

38. The three-dimensional crosslinked hydrogel composition as defined in claim 29, further comprising cells incorporated into the hydrogel composition, thereby forming a hydrogel/cell system.

39. The three-dimensional crosslinked hydrogel composition as defined in claim 29 wherein when the predetermined calcium ion concentration is between about 0.0005 M and about 0.0010 M, the hydrogel composition swelled.

40. The three-dimensional crosslinked hydrogel composition as defined in claim 29 wherein when the predetermined calcium ion concentration is about 0.0040 M, the hydrogel composition shrank.

41. The method as defined in claim 1 wherein the three-dimensional crosslinked hydrogel system is structurally homogeneous.

42. The three-dimensional crosslinked hydrogel composition as defined in claim 29 wherein the composition is structurally homogeneous.

43. The method as defined in claim 1 wherein the source of calcium ions is in powder form.

44. The three-dimensional crosslinked hydrogel composition as defined in claim 26 wherein the source of calcium cations is in powder form.

45. A method for preparing a three-dimensional hydrogel system, the method comprising the steps of:
adding a calcium-releasing compound to a mixture of at least one hydrophilic polymer comprising an alginate salt and a source of calcium cations to provide a three-dimensional crosslinked hydrogel system, wherein the calcium releasing compound is D-glucono- δ-lactone, wherein the alginate salt is selected from the group consisting of sodium alginate and potassium alginate, and wherein the source of calcium ions is selected from the group consisting of calcium carbonate, calcium sulfate, and calcium sulfate dihydrate; and selectively controlling shrinking, swelling or maintaining of the hydrogel system by varying a calcium ion concentration of a separate medium into which the hydrogel system is introduced, wherein the hydrogel system swelled at calcium ion concentrations between about 0.0005 M and about 0.0010 M; wherein the hydrogel system shrank at a calcium ion concentration of about 0.0040 M; and wherein the hydrogel system remained substantially the same size at calcium ion concentrations between about 0.0020 M and about 0.0030 M;

wherein the three-dimensional crosslinked hydrogel system has a calcium ion to carboxyl molar ratio ranging between about 0.09 and about 0.9.

46. The method as defined in claim 45 wherein the source of calcium ions is calcium carbonate, and wherein the molar ratio of the calcium carbonate to the D-glucono-δ-lactone is 0.5.

47. The method as defined in claim 46 wherein the calcium ion to carboxyl molar ratio ranges between about 0.18 and about 0.72.

48. The method as defined in claim 47, further comprising the step of culturing the three-dimensional crosslinked hydrogel system in the medium for growing cells in vitro.

49. The composition as defined in claim 38 wherein the cells are at least one of osteoblasts and cells which secrete a medically useful compound.

* * * * *